United States Patent
KenKnight et al.

[19]

[11] Patent Number: 5,916,243
[45] Date of Patent: Jun. 29, 1999

[54] IMPLANTABLE CONFORMAL COIL PATCH ELECTRODE WITH MULTIPLE CONDUCTIVE ELEMENTS FOR CARDIOVERSION AND DEFIBRILLATION

[75] Inventors: Bruce H. KenKnight, Minneapolis; Roger W. Dahl, Andover, both of Minn.; David K. Swanson, Mountain View, Calif.

[73] Assignee: Cardiac Pacemakers, Inc., St. Paul, Minn.

[21] Appl. No.: 08/609,215

[22] Filed: Mar. 1, 1996

Related U.S. Application Data

[63] Continuation of application No. 07/980,843, Nov. 24, 1992, Pat. No. 5,496,362.

[51] Int. Cl.$^6$ ............................................. A61N 1/05
[52] U.S. Cl. ............................................................. 607/129
[58] Field of Search .................................... 607/374, 375, 607/119, 122, 129, 130, 132

[56] References Cited

U.S. PATENT DOCUMENTS

| | | |
|---|---|---|
| 3,804,098 | 4/1974 | Friedman . |
| 3,942,536 | 3/1976 | Mirowski et al. . |
| 4,030,508 | 6/1977 | Thalen . |
| 4,030,509 | 6/1977 | Heilman et al. . |
| 4,106,512 | 8/1978 | Bisping . |
| 4,136,703 | 1/1979 | Wittkampf . |
| 4,217,913 | 8/1980 | Dutcher . |
| 4,270,549 | 6/1981 | Heilman . |
| 4,291,707 | 9/1981 | Heilman et al. . |
| 4,311,153 | 1/1982 | Smits . |
| 4,463,765 | 8/1984 | Gold . |
| 4,548,203 | 10/1985 | Tacker, Jr. et al. . |
| 4,559,951 | 12/1985 | Dahl et al. . |
| 4,567,900 | 2/1986 | Moore . |
| 4,570,642 | 2/1986 | Kane et al. . |
| 4,603,705 | 8/1986 | Speicher et al. . |
| 4,624,265 | 11/1986 | Grassi . |
| 4,624,266 | 11/1986 | Kane . |
| 4,627,439 | 12/1986 | Harris . |
| 4,633,880 | 1/1987 | Osypka et al. . |
| 4,646,755 | 3/1987 | Kane . |
| 4,649,938 | 3/1987 | McArthur . |
| 4,662,377 | 5/1987 | Heilman et al. . |

(List continued on next page.)

FOREIGN PATENT DOCUMENTS

| | | |
|---|---|---|
| 0057877 | 8/1982 | European Pat. Off. ............... 607/121 |
| 211 166 | 5/1986 | European Pat. Off. . |
| 0211166 | 2/1987 | European Pat. Off. . |
| 0452278 | 10/1991 | European Pat. Off. ......... A61N 1/05 |
| 0460324 | 12/1991 | European Pat. Off. . |
| 0612538 | 8/1994 | European Pat. Off. ....................... 1/5 |
| 0672431 | 9/1995 | European Pat. Off. ......... A61N 1/05 |
| 2588758 | 4/1987 | France . |
| 3-168161 | 7/1991 | Japan . |
| 4-40966 | 2/1992 | Japan . |
| 2032278 | 6/1980 | United Kingdom ................... 607/122 |
| 89/06148 | 7/1989 | WIPO . |
| 92/07616 | 5/1992 | WIPO . |

OTHER PUBLICATIONS

Fain, et al., "A New Internal Defibrillation Lead System: Intrapericardial Placement Without Thoracotomy", *Abstracts Circulation*, 76, Suppl. IV, 1839, (Oct. 1987).

Jones, D.L., et al., "Internal Cardiac Defibrillation in Man: Pronounced Improvement with Sequential Pulse Delivery to Two Different Lead Orientations", *Circulation, vol. 73, No. 3*, pp. 484–491, (Mar. 1986).

*Primary Examiner*—Jeffrey R. Jastrzab
*Attorney, Agent, or Firm*—Schwegman, Lundberg, Woessner & Kluth, P.A.

[57] ABSTRACT

Body-implantable leads with open, unbacked (uninsulated) electrode structures having electrical discharge surfaces formed by conductive elements, such as mesh and braid, and preferably coils. The electrode structures can be classified by pattern: (1) loops, (2) linear arrays and (3) radial arrays. The electrodes are located on or near the epicardial surface of the right and left heart.

5 Claims, 22 Drawing Sheets

U.S. PATENT DOCUMENTS

| | | |
|---|---|---|
| 4,664,113 | 5/1987 | Frisbie et al. . |
| 4,727,877 | 3/1988 | Kallok . |
| 4,784,161 | 11/1988 | Skalsky et al. . |
| 4,799,486 | 1/1989 | DuFault . |
| 4,799,493 | 1/1989 | DuFault . |
| 4,817,608 | 4/1989 | Shapland et al. . |
| 4,817,634 | 4/1989 | Holleman et al. . |
| 4,819,661 | 4/1989 | Heil, Jr. et al. . |
| 4,819,662 | 4/1989 | Heil, Jr. et al. . |
| 4,827,932 | 5/1989 | Ideker et al. . |
| 4,860,769 | 8/1989 | Fogarty et al. . |
| 4,865,037 | 9/1989 | Chin et al. . |
| 4,886,074 | 12/1989 | Bisping . |
| 4,905,691 | 3/1990 | Rydell ............................. 606/47 |
| 4,924,881 | 5/1990 | Brewer . |
| 4,938,231 | 7/1990 | Milijasevic et al. . |
| 4,944,300 | 7/1990 | Saksena . |
| 4,953,551 | 9/1990 | Mehra et al. . |
| 4,967,766 | 11/1990 | Bradshaw . |
| 4,971,070 | 11/1990 | Holleman et al. . |
| 4,998,975 | 3/1991 | Cohen et al. . |
| 5,016,645 | 5/1991 | Williams et al. . |
| 5,016,646 | 5/1991 | Gotthardt et al. . |
| 5,016,808 | 5/1991 | Heil, Jr. et al. . |
| 5,020,544 | 6/1991 | Dahl et al. . |
| 5,044,375 | 9/1991 | Bach, Jr. et al. . |
| 5,050,601 | 9/1991 | Kupersmith et al. . |
| 5,056,516 | 10/1991 | Spehr . |
| 5,063,932 | 11/1991 | Dahl et al. . |
| 5,076,285 | 12/1991 | Hess et al. . |
| 5,083,562 | 1/1992 | de Coriolis et al. . |
| 5,105,826 | 4/1992 | Smits et al. . |
| 5,107,834 | 4/1992 | Ideker et al. . |
| 5,111,811 | 5/1992 | Smits . |
| 5,111,812 | 5/1992 | Swanson et al. . |
| 5,129,404 | 7/1992 | Spehr . |
| 5,133,353 | 7/1992 | Hauser . |
| 5,133,365 | 7/1992 | Heil, Jr. et al. . |
| 5,152,299 | 10/1992 | Soukup . |
| 5,165,403 | 11/1992 | Mehra . |
| 5,174,303 | 12/1992 | Schroeppel . |
| 5,203,348 | 4/1993 | Dahl et al. ............................. 607/129 |
| 5,209,229 | 5/1993 | Gilli . |
| 5,230,337 | 7/1993 | Dahl et al. ............................. 607/119 |
| 5,259,394 | 11/1993 | Bens ............................. 607/127 |
| 5,259,395 | 11/1993 | Li ............................. 607/131 |
| 5,261,400 | 11/1993 | Bardy ............................. 607/5 |
| 5,269,319 | 12/1993 | Schulte et al. . |
| 5,271,417 | 12/1993 | Swanson et al. ............................. 607/122 |
| 5,282,845 | 2/1994 | Bush et al. ............................. 607/128 |
| 5,300,108 | 4/1994 | Rebell et al. ............................. 607/127 |
| 5,300,110 | 4/1994 | Latterell et al. ............................. 607/130 |
| 5,314,459 | 5/1994 | Swanson et al. ............................. 607/122 |
| 5,324,327 | 6/1994 | Cohen ............................. 607/122 |
| 5,342,414 | 8/1994 | Mehra ............................. 607/127 |
| 5,344,439 | 9/1994 | Otten ............................. 607/126 |
| 5,358,516 | 10/1994 | Myers et al. ............................. 607/116 |
| 5,366,496 | 11/1994 | Dahl et al. ............................. 607/132 |
| 5,374,286 | 12/1994 | Morris ............................. 607/119 |
| 5,397,342 | 3/1995 | Heil, Jr. et al. ............................. 607/129 |
| 5,405,373 | 4/1995 | Petersson, et al. ............................. 607/121 |
| 5,411,544 | 5/1995 | Mar, et al. ............................. 607/122 |
| 5,425,755 | 6/1995 | Doan ............................. 607/119 |
| 5,425,756 | 6/1995 | Heil, Jr. et al. ............................. 607/128 |
| 5,447,533 | 9/1995 | Vachon et al. ............................. 607/120 |
| 5,447,534 | 9/1995 | Jammet ............................. 607/127 |
| 5,456,706 | 10/1995 | Pless et al. ............................. 607/122 |
| 5,456,708 | 10/1995 | Doan et al. ............................. 607/127 |
| 5,476,501 | 12/1995 | Stewart et al. ............................. 607/127 |
| 5,492,119 | 2/1996 | Abrams . |
| 5,500,008 | 3/1996 | Fain ............................. 607/5 |
| 5,522,874 | 6/1996 | Gates ............................. 607/127 |
| 5,531,780 | 7/1996 | Vachon ............................. 607/120 |
| 5,534,022 | 7/1996 | Hoffmann et al. ............................. 607/122 |
| 5,545,205 | 8/1996 | Schulte et al. ............................. 607/123 |
| 5,554,178 | 9/1996 | Dahl et al. ............................. 607/122 |
| 5,578,068 | 11/1996 | Laske et al. ............................. 607/126 |

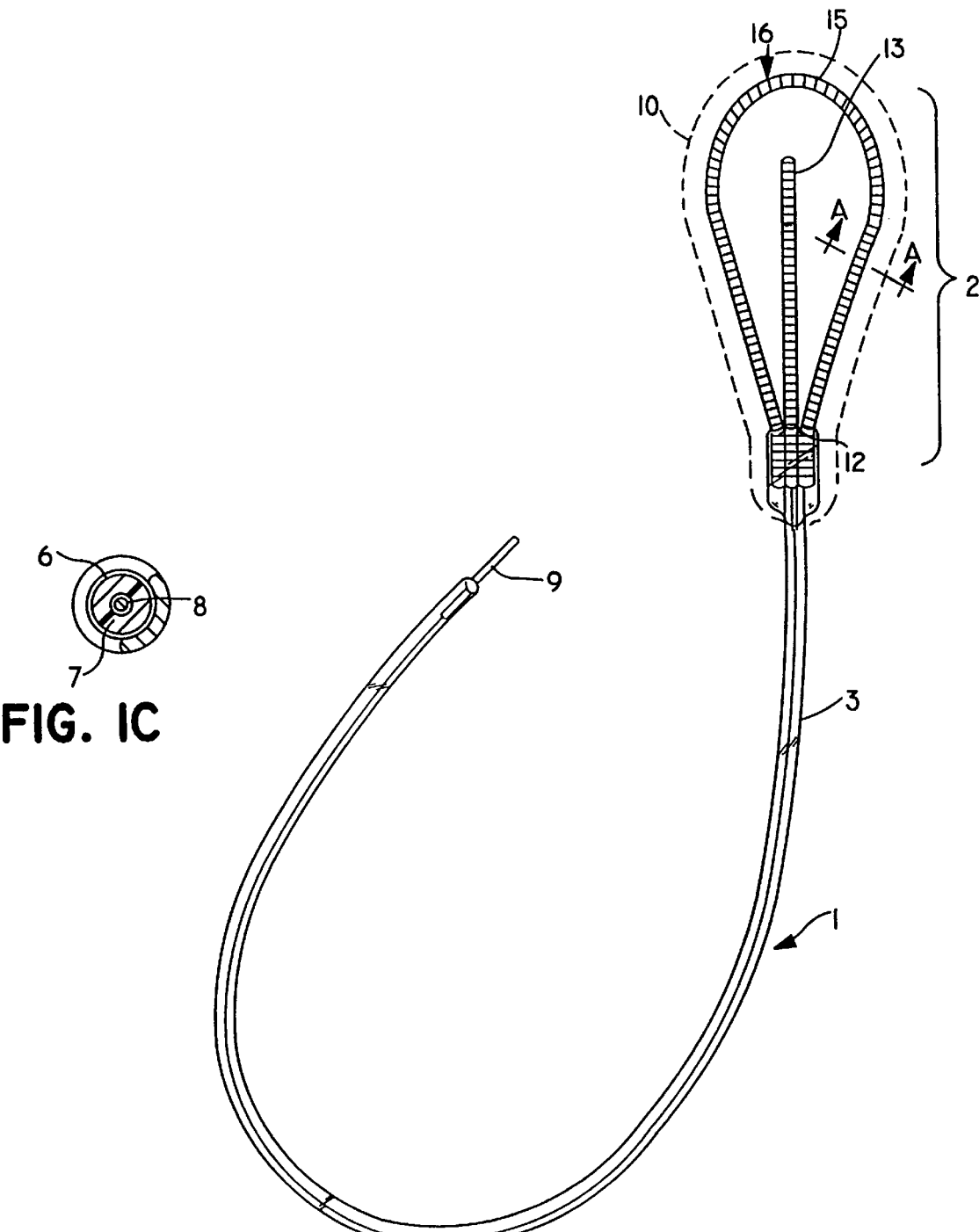

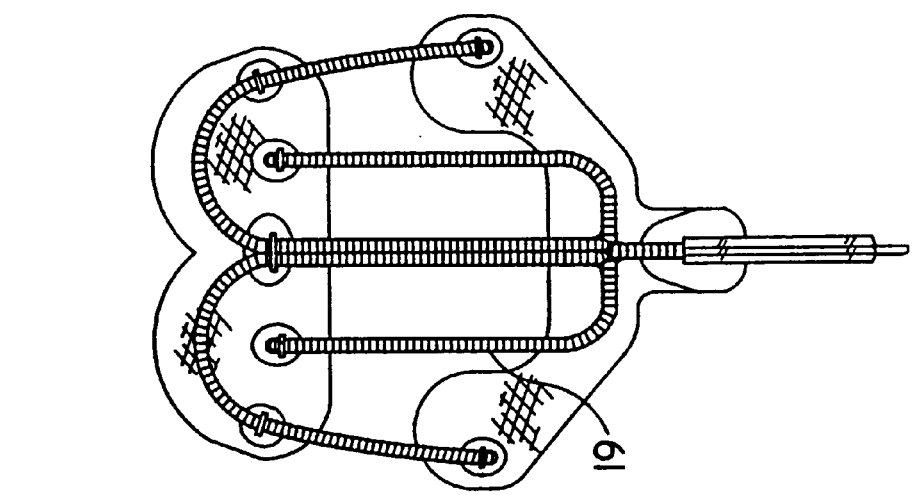
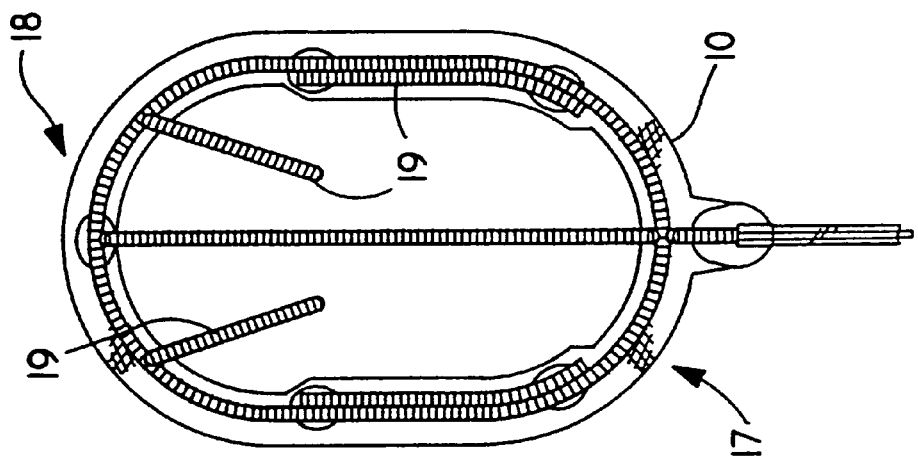
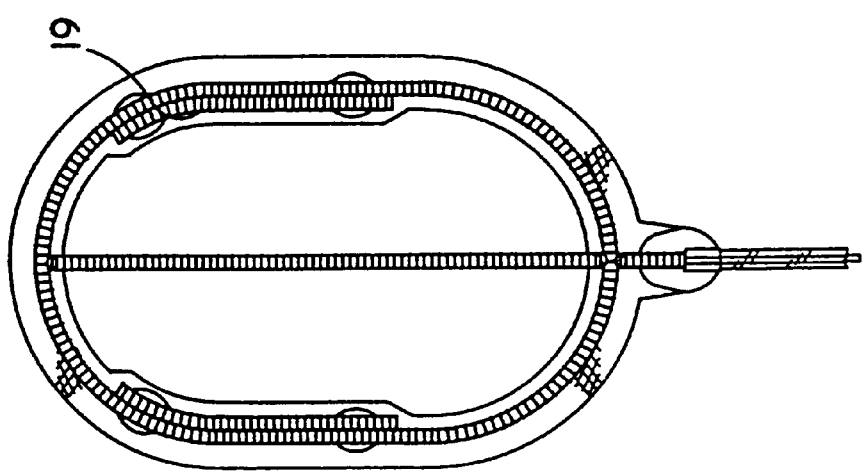

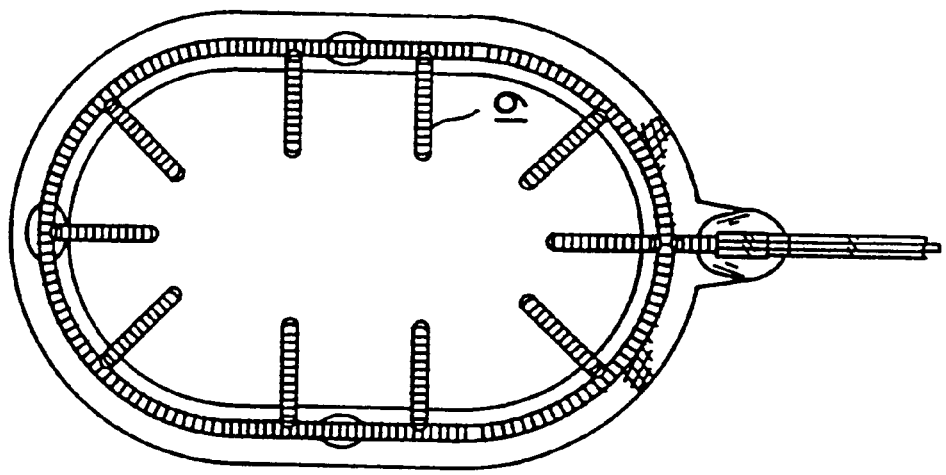
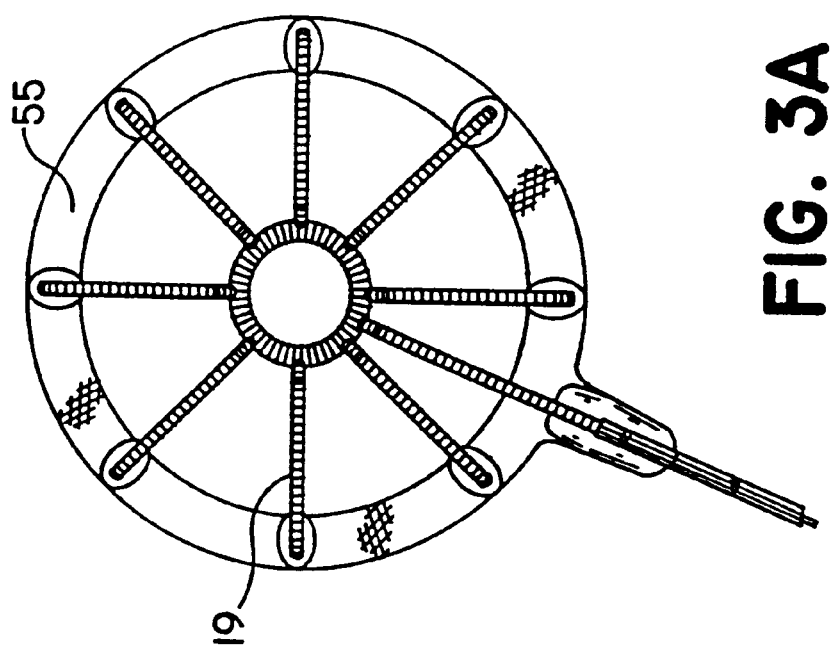

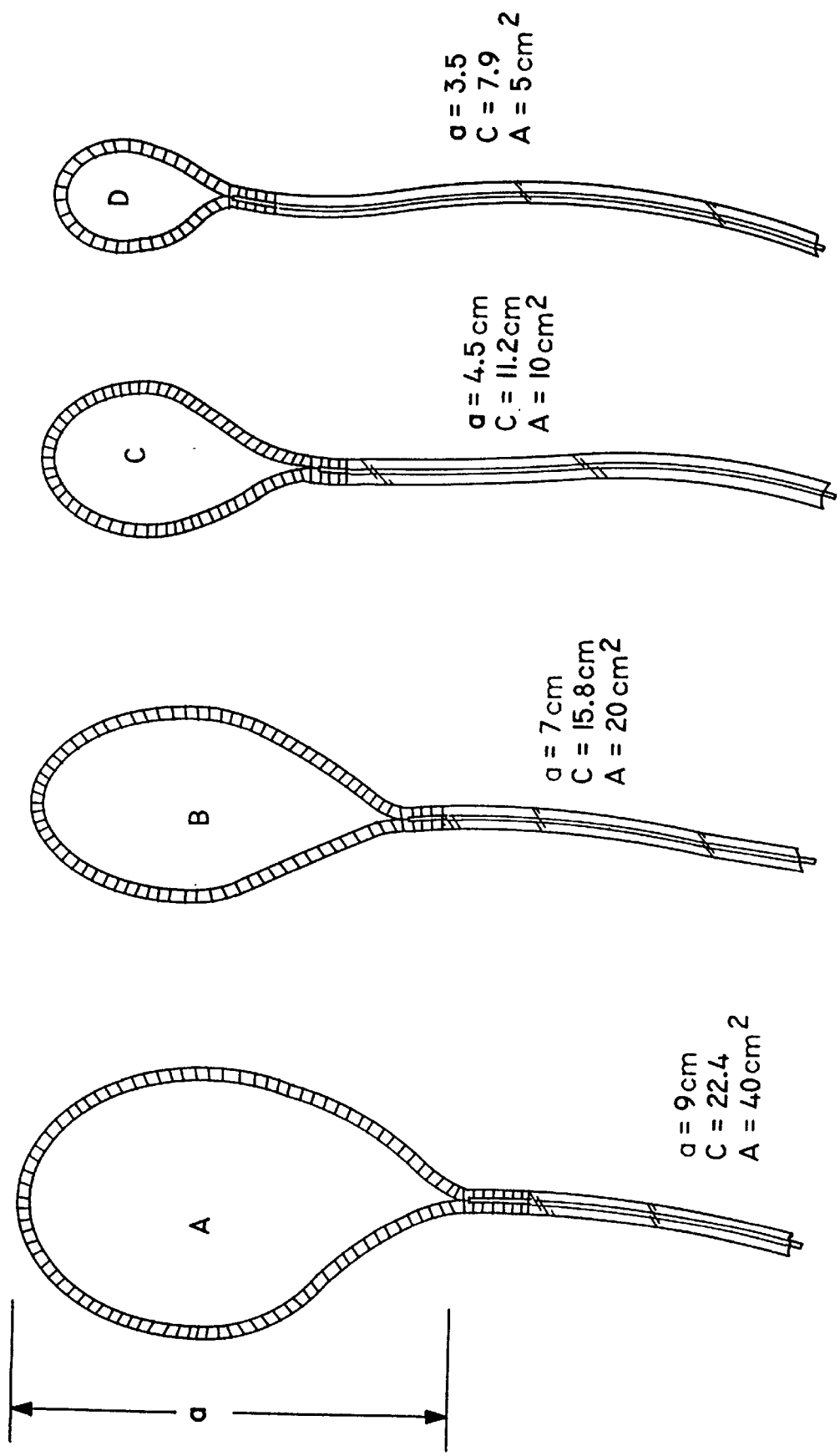

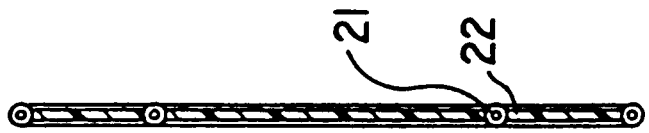
FIG. 9A"
FIG. 9A'
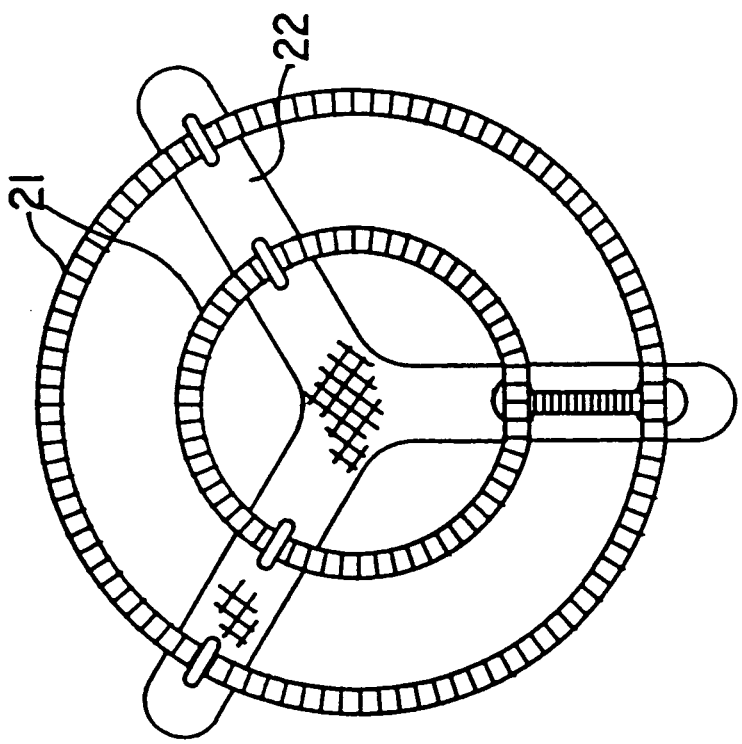
FIG. 9A

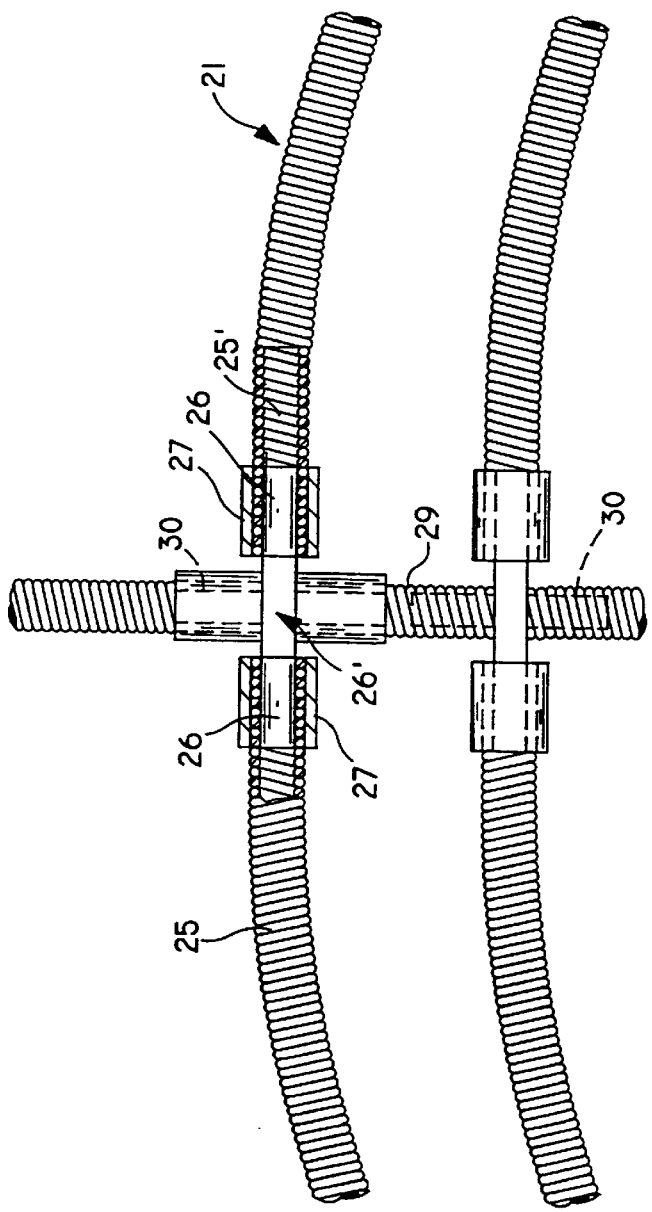
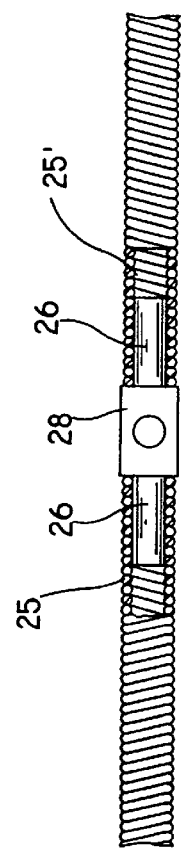
FIG. 9D
FIG. 9E

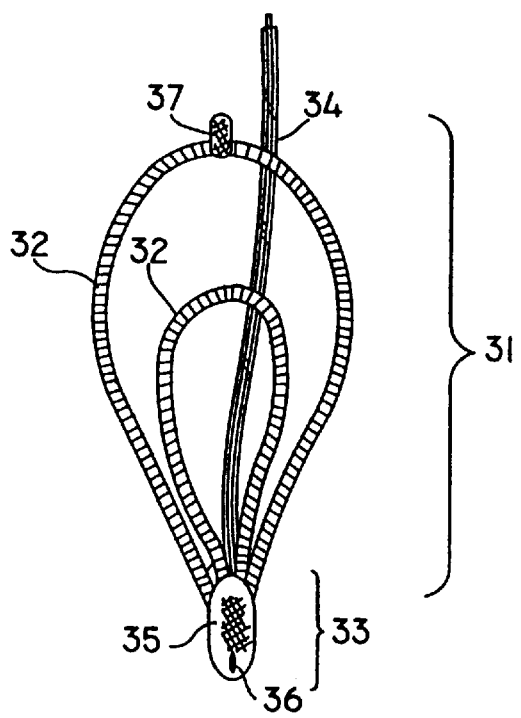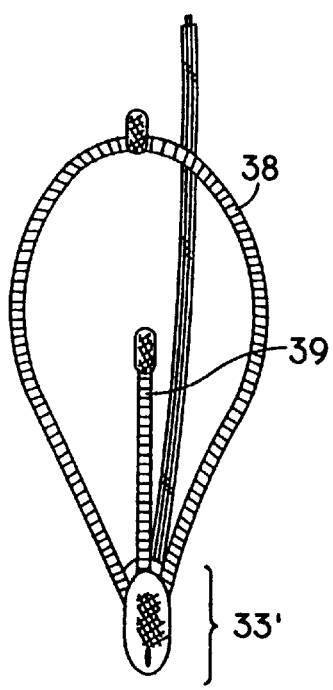
FIG. 10A  FIG. 10A'

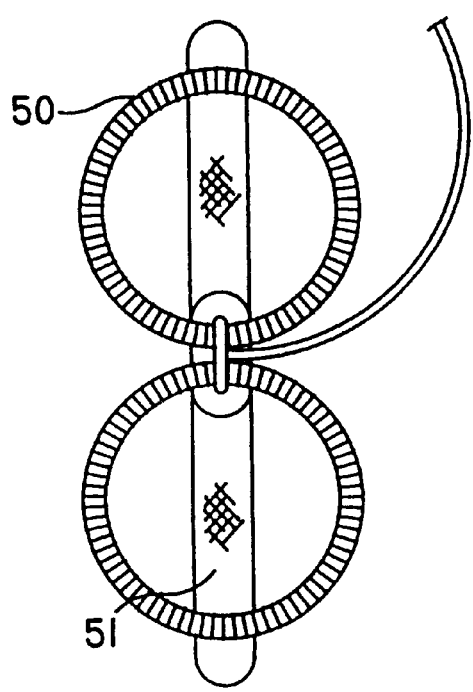 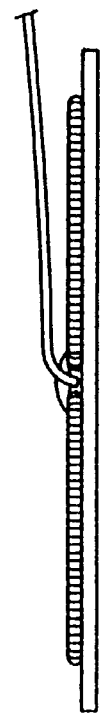
FIG. IIA  FIG. IIA'

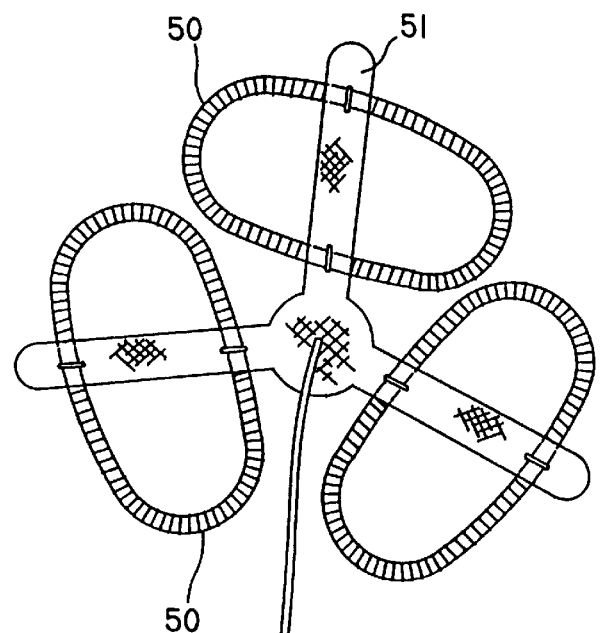
FIG. IIB
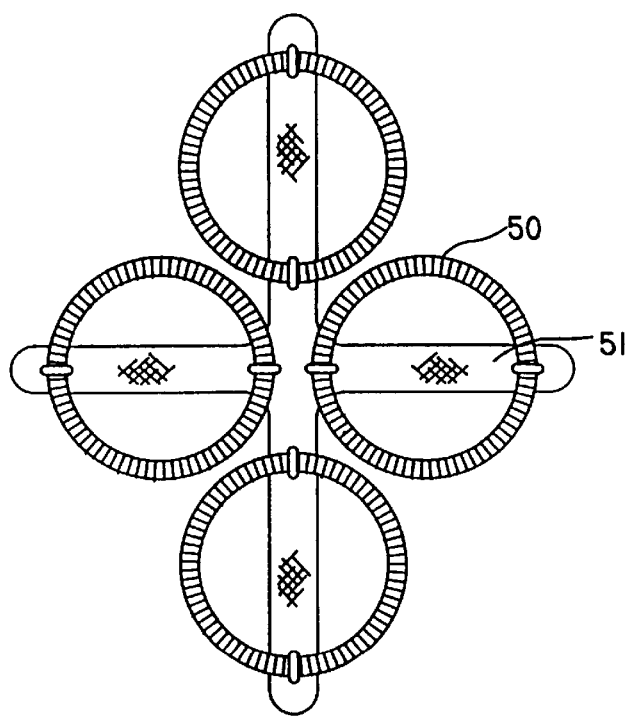
FIG. IIC

IMPLANTABLE CONFORMAL COIL PATCH ELECTRODE WITH MULTIPLE CONDUCTIVE ELEMENTS FOR CARDIOVERSION AND DEFIBRILLATION

CROSS-REFERENCE TO RELATED APPLICATIONS

This is a continuation of application Ser. No. 07/980,843, filed Nov. 24, 1992 now U.S. Pat. No. 5,496,362.

FIELD OF THE INVENTION

The present invention relates to the field of implantable conformal coil patch electrodes with multiple conductive elements for cardioversion, defibrillation and tachyrhythmia therapy.

BACKGROUND OF THE INVENTION

Many different electrodes and electrode configurations have been disclosed for applying electrical currents to the heart in an attempt to produce the most efficacious therapy and the least deleterious shock-induced alteration of myocardial electro-physiologic function. These electrodes have been placed directly on the epicardium of the heart, within the chambers of the right atrium and ventricle, in the coronary sinus, in the venae proximal to the right heart and in the left lateral thoracic subcutis. Various physical and electrical combinations of these electrodes form the electrode configuration.

In the past, the electrode configuration, as described above, most frequently employed in patients has been the epicardial patch-to-patch configuration as disclosed in U.S. Pat. No. 4,291,707 to Heilman et al. This prior art patch is bulky and relatively inflexible; the electrode is backed with an insulating layer of silicone rubber that increases transthoracic defibrillation shock strength requirements as reported by B. B. Lerman and O. C. Deale in *Circulation* 1990; 81:1409–1414.

More recently, a non-thoracotomy electrode configuration combining endocardial catheter electrodes with a mesh patch located in the left axillary subcutis was disclosed in U.S. Pat. No. 4,662,337 to Heilman, et al.

Still further potential disadvantages of the catheterpatch configuration are related to the impedance of the current pathway and the non-uniformity of the shock-induced electric field. High impedance pathways require higher shock intensities to defibrillate.

Prior art deployable epicardial defibrillation electrodes such as those disclosed in U.S. Pat. No. 4,567,900 to Moore undergo shape conversion subsequent to electrode placement. However, this design is believed to be fraught with problems related to structural frailty and it does not address either the problem of nonuniform current density at the electrode perimeter or fixation to adjacent tissues.

Additional disadvantages of prior art electrodes include excessive size, insufficient surface area, inefficient conductive discharge surfaces, excessive stiffness, nonconformity to heart shape, fatigue fracture, complex geometries, and complicated and hazardous implantation schemes.

Discussion in U.S. Pat. No. 5,016,645 to Willams et al. and U.S. Pat. No. 4,827,932 to Ideker et al. states either explicitly or implicitly that nonconductive backing of the defibrillation electrodes is necessary or beneficial to prevent shunting.

According to the present invention an opposite effect is realized, that is, unbacked structures require lower shock strengths for defibrillation than similar structures backed with a nonconductive material.

SUMMARY OF THE INVENTION

The invention relates to the use of body-implantable leads with open, unbacked (uninsulated) electrode structures having electrical discharge surfaces formed by conductive elements, such as mesh and braid, and preferably coils. To improve descriptive clarification, the electrode structures can be classified by pattern formed by the conductive discharge surfaces: (1) loops, (2) linear arrays and (3) radial arrays.

In the present invention, the electrodes can be located on or near the epicardial surface of the right and left heart, thereby eliminating problems associated with other so-called non-thoracotomy electrode configurations involving right heart endocardial electrode(s) (e.g. superior vena cava syndrome, pulmonary embolism, endocardial shock-induced tissue damage, endocarditis, physical interference with existing or future pacing leads) and left thorax subcutaneous patch(es) (e.g. patient discomfort, fatigue fracture, transcutaneous erosion, subcutaneous infection). Electrodes of the present invention may be placed intrapericardially or extrapericardially.

In general, the present invention is used to efficiently distribute electrical current from implantable cardioverter/defibrillators for treatment of ventricular fibrillation or hemodynamically stable or unstable ventricular tachyarhythmias. The present invention solves several problems related to current epicardial (the location of electrodes in direct contact with the epimyocardial surface and those attached to the parietal pericardium) electrode systems known in the art of implantable defibrillation.

First, the invention reduces inhibition of heart wall motion by exhibiting low stiffness and high flexibility.

Second, the invention reduces therapeutic shock strength requirements by distributing the current over more efficient conductive discharge surfaces and thereby reducing shock impedance.

Third, the invention reduces an undesirable increase in transthoracic defibrillation strength requirements because the open structure (an absence of any electrically insulative backing material) does not insulate large portions of both ventricles.

Fourth, the invention exhibits better mechanical fatigue resistance to repeated flexure produced during normal cardiac contraction.

And fifth, the invention, in several embodiments, can be implanted using so-called "minimally-invasive" approaches involving cardiac access through subxiphoid, subcostal and/or intercostal incisions.

Experimentation with these types of electrodes has shown a significant reduction of shock strength (peak voltage and energy delivered) for defibrillation compared to the conventional mesh patch as embodied in the Heilman et al patents.

BRIEF DESCRIPTION OF THE DRAWINGS

FIG. 1B illustrates an insulated lead body and conductive electrode portion.

FIG. 1C is a sectional view taken along line A—A of FIG. 1B.

FIGS. 2A–2E illustrate linear array conductive electrodes.

FIGS. 3A–3D illustrate radial array conductive electrodes.

FIGS. 8A–8D illustrates four conductive loop electrodes of varying circumscribed area.

FIGS. 11A, 11B and 11C illustrate spatially-isolated coil loop conductive electrodes.

FIG. 11A' is a side view of FIG. 11A.

DETAILED DESCRIPTION OF THE PREFERRED EMBODIMENTS

Figure 1A:
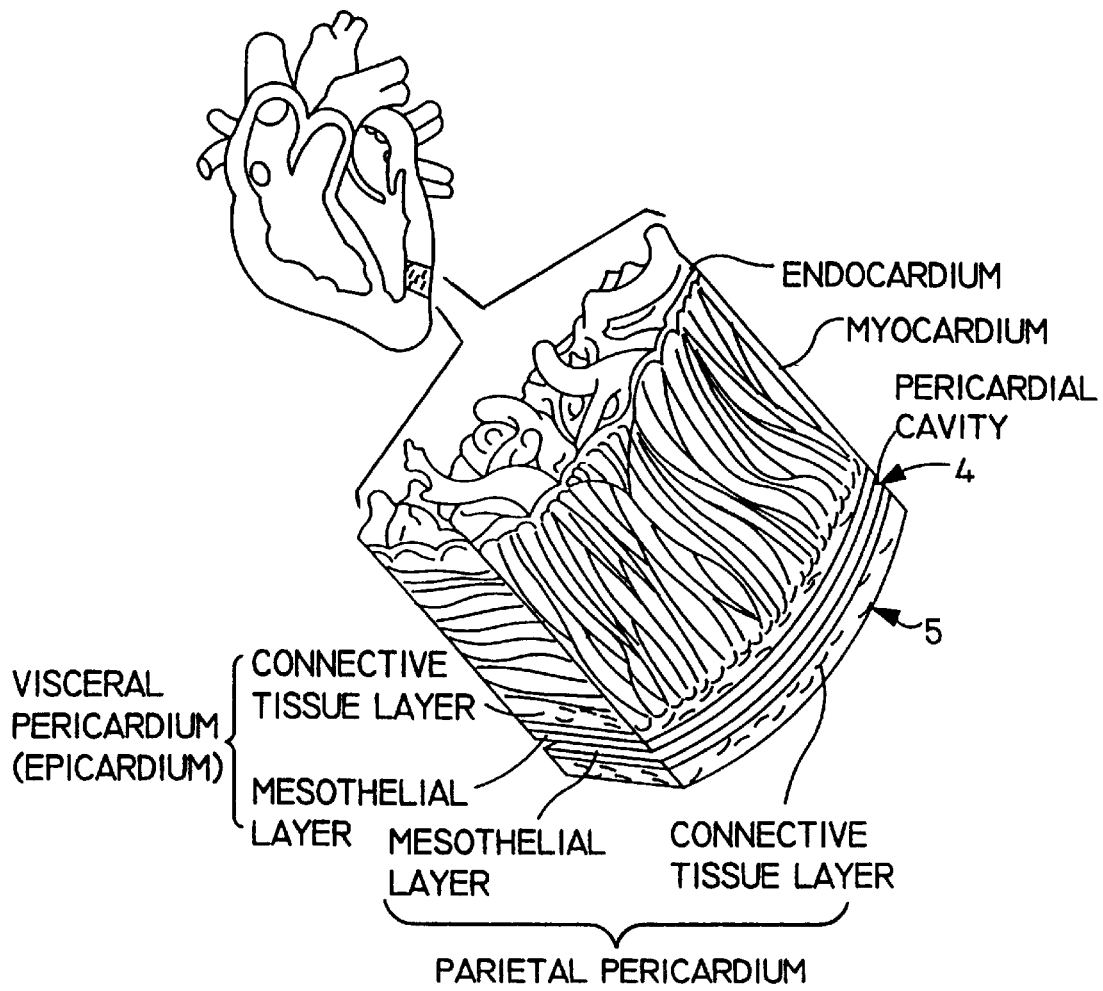
FIG. 1A is an enlarged view of a section of the heart structure.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

By the present invention, conductive electrode structures include conductive coils forming a conductive discharge surface with an optional insulative backing, preferably on one side of the electrode structure. The insulative backing is preferably located on the side of the electrode structure facing away from the heart.

The conductive electrode structures are formed, for example, (1) as a peripheral loop, optionally having a single radially inwardly extending conductive element, (2) as linear arrays having conductive elements extending parallel to or perpendicular to a longitudinal axis of the electrode structure, (3) as radial arrays having elements extending radially inwardly or radially outwardly, (4) as concentric loop structures, (5) as eccentric loop structures, and (6) as spatially isolated coil loop structures.

FIGS. 1 to 3 show embodiments of leads with conductive electrode structures. They are intended to serve as representative examples and do not exhaustively define all parameters meant to be covered by the spirit of the present invention.

Figure 2F:
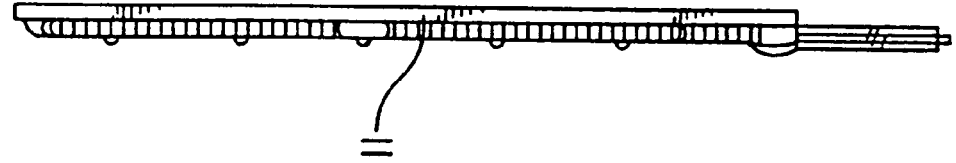
FIG. 2F is a side view of the conductive electrode shown in FIG. 2E.

Each lead possesses several common characteristics. With reference to FIGS. 1 to 3 and 8 to 11, as shown in FIG. 1B, the lead 1 is formed by a conductive electrode portion 2 (distal) mounted at one terminal end of an insulated lead body 3 (proximal). The electrode portion 2 is formed by conductive metallic elements (normally helically-wound multifilar coils) that are electrically common. The electrode portion is designed to be positioned on or near the heart structure, either intra-pericardially 4 or extra-pericardially 5, as shown in FIG. 1A.

The metallic coil(s) comprising the electrode portion are either contiguous or spatially isolated to form two or more elements that form the conductive discharge surface. As shown in FIG. 1C, the lumen 6 of the metallic coil(s) are filled with silicone tubing 7 or a solid cylindrical form of silicone through which a drawn brazed stranded (DBS) conductor 8 can pass to carry the shock currents to various terminations on the electrode portion.

The electrode portion is energized with an implantable cardioverter defibrillator pulse generator (not shown) by applying a potential at the proximal terminal pin 9 located at an opposite terminal end of lead body 3 from electrode portion 2. Reinforced silicone sheet 10 may be used to form a narrow (<1 cm) rim or boundary that defines the perimeter of the electrode portion, as in FIGS. 1B (phantom lines) and 2B, for example, on a side of the electrode facing away from the heart. Alternatively, this rim could be formed by a silicone covered coil of appropriate stiffness.

This rim defines the electrode perimeter and serves several purposes: (1) it adds structural stability to the electrode structure by "tieing" together the ends of the conductive elements, and (2) it provides reliable means for securing sutures to the electrode during immobilization of the electrode on or near the heart. Alternatively, adequate structural integrity could be imparted to the electrode on a side of the electrode facing away from the heart by means of a fabric backing 11 (FIGS. 2E and 2F) that is porous and offers negligible electrical resistance during therapeutic shocks.

FIG. 1B shows a preferred embodiment of a coil patch electrode classified as a "loop". The loop is formed by deflecting the coil 15 180° and securing it to the distal end of the lead body 3, here referred to as the root 12 of the loop. An electrically common element 13 proceeds radially inward from the root 12 toward the distal extreme of the loop, here referred to as the apex 16 of the loop. This inner common element 13 carries current from the electrode boundary to inner regions of the loop thereby increasing the shock field strength in heart tissue near the center of the loop which otherwise would have experienced weak shock fields. The loop illustrated in FIG. 1B may be a single, multiple concentric, multiple eccentric or multiple spatially isolated loop as shown in FIGS. 8 to 11.

Figure 2E:
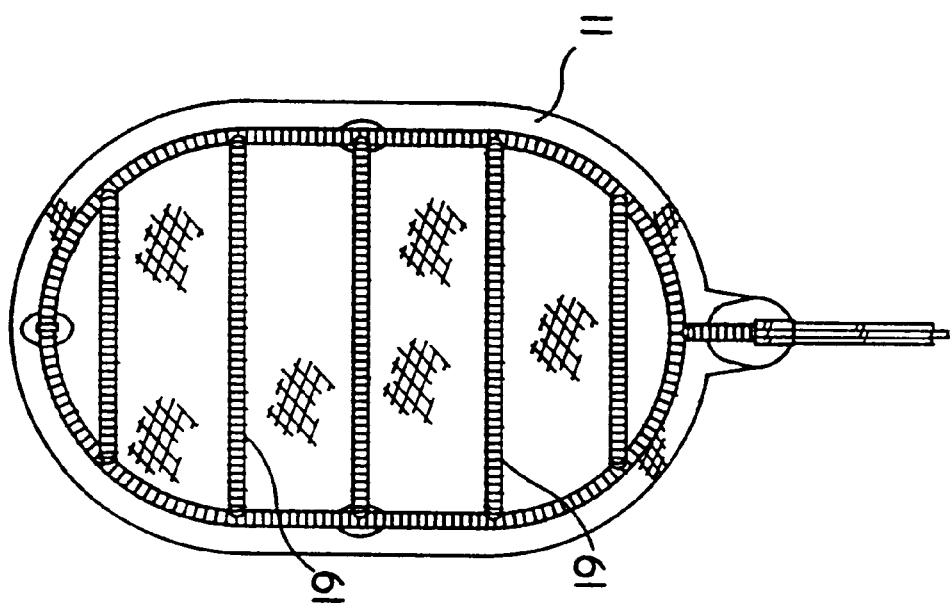
Figure 2D:
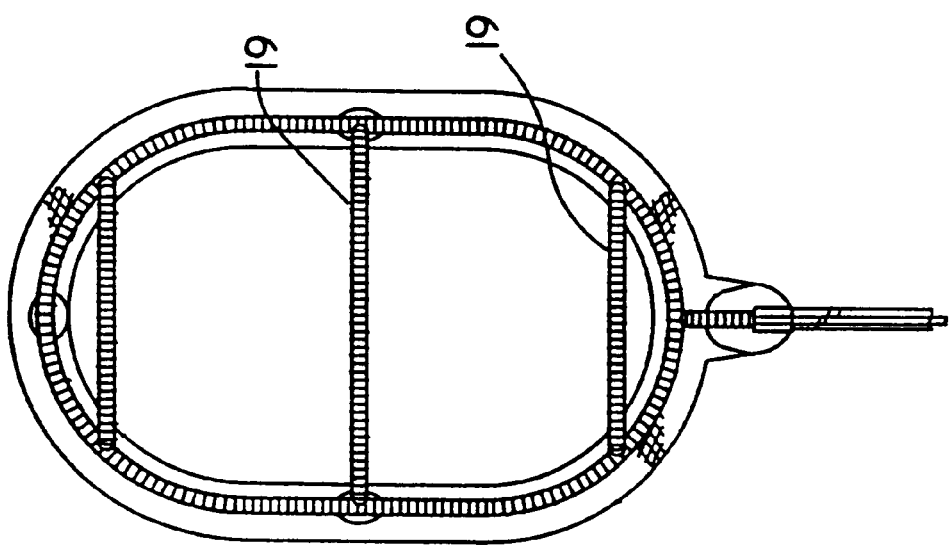

FIGS. 2A to 2E illustrate various embodiments associated with conformal coil patches classified as "linear arrays". Linear arrays are grouped by the orientation of the conductive elements 19 relative to the long axis of the patch: (1) arrays with elements 19 substantially parallel to the longitudinal axis of the patch are considered "vertical", (FIGS. 2A, 2B and 2C) while (2) arrays with elements 19 substantially perpendicular to the long axis of the patch are considered "transverse" (FIGS. 2D and 2E).

A preferred embodiment is shown in FIG. 2B. The shape of the perimeter is formed by connecting tangent points from two half-circles with equal or unequal radii resulting in a structural boundary that can be referred to as oval (equal radii) or "egg-shaped" (unequal radii). This shape conforms well to the heart with the large radii end 17 positioned at the cardiac base and the small radii end 18 positioned at the cardiac apex.

With reference to FIG. 2C, three or more conductive coil elements 19 are spatially isolated in an interdigitating pattern as shown. The benefit of interdigitation is related to separating regions of high current density. The optimum number of elements results in lowest shock strength requirements for defibrillation.

Unlike embodiments shown in FIGS. 2A, 2B, 2D and 2E, the electrode structure of FIG. 2C is not bounded by a silicone sheet perimeter. Structural stability is maintained by incorporating biasing means (spring wire or premolded silicone cylindrical forms) within the coil interior.

Figure 3D:
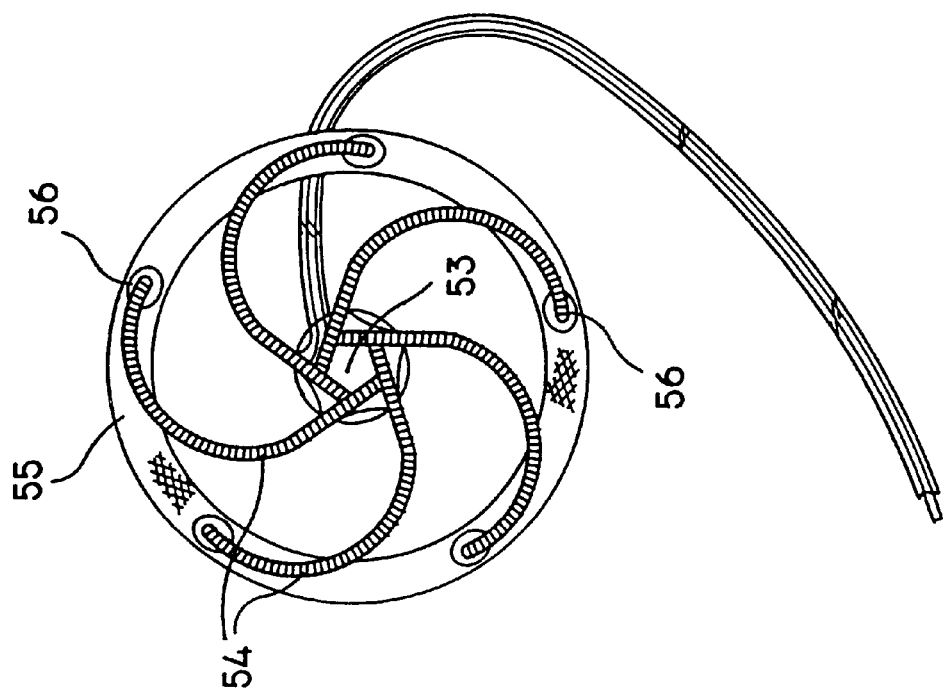
Figure 3C:
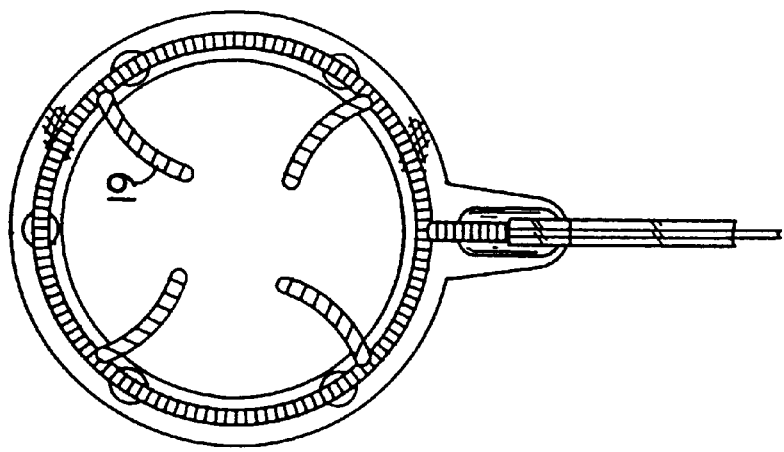

FIGS. 3A to 3D show various embodiments of patches classified as "radial arrays". Radial arrays are grouped by the location of the elements: (1) arrays with elements emanating from the center outward to a radially outermost boundary are considered "type 1", (FIGS. 3A and 3D) while (2) arrays with elements proceeding from the boundary partially inward are considered "type 2" (FIGS. 3B and 3C). Electrical connection to the discharge surface is preferably made at the center 20 of the electrode for "type 1" radial arrays and at the perimeter for "type 2" arrays.

In FIG. 3D a centralized hub portion 53 freely "floats" during ventricular contractions as a consequence of the highly compliant involuted conductive elements 54. A perimeter structure 55 provides a stable but resilient platform on which the terminal ends 56 of the conductive elements terminate and are bonded, thereby maintaining element separation.

In general, an open structure (not backed by an insulator) allows fibrotic isolation of individual elements that reduces the likelihood of structural deformation (element migration) during capsular contraction. The perimeter 55 can be constructed from die-cut silicone rubber sheeting, molded in one piece from a suitable material such as silicone rubber or fabricated by covering a coil with silicone tubing. In either case, all terminal coil ends 56 are covered with silicone to protect underlying tissues. The curved coil conductive elements 54 forming the conductive discharge surface proceed in an involuted pattern, from the inner hub 53 to the outer perimeter 55 in a clockwise manner and are uninsulated everywhere except at the hub and at the ends. Alternatively, the elements may "swirl" counter-clockwise.

The preferred relaxed electrode shape or element pattern for any of the embodiments shown need not be symmetric. Element lengths, spacings, positions and orientations may be changed to optimize the shock-induced voltage gradient distribution in and around the heart.

Embodiments of the present invention may be implanted by several means: (1) direct cardiac exposure through sternotomy or thoracotomy followed by surgical attachment to epicardium or parietal pericardium, (2) physically urging the electrode through an introducing conduit positioned across the chest wall and in some procedures within the pericardial space using minimally invasive techniques involving subxiphoid, subcostal or thoracoscopic-assisted intercostal approaches. Further urging of the electrode through and out of the introducing conduit results in separation of the electrode elements by release of strain energy previously imparted to the intra-electrode biasing means. During this electrode shape change, the pericardium assists the electrode positioning process by acting as a "sock" to bear against the electrode and direct its translation along the epicardial surface. Stability of the final electrode shape and position is achieved by anchoring the electrode to suitable adjacent tissues with sutures, staples or with an active fixation means (not shown). (3) Alternatively, the electrodes may be implanted and secured to the parietal pericardium (extrapericardial or sometimes referred to as retropericardial) through a small intercostal defect using thoracoscopic assistance. In this case, the ipsilateral lung may be deflated to increase cardiac exposure. The electrodes are positioned on or near the heart and secured to the underlying tissues with sutures or metallic staples.

Figure 4:
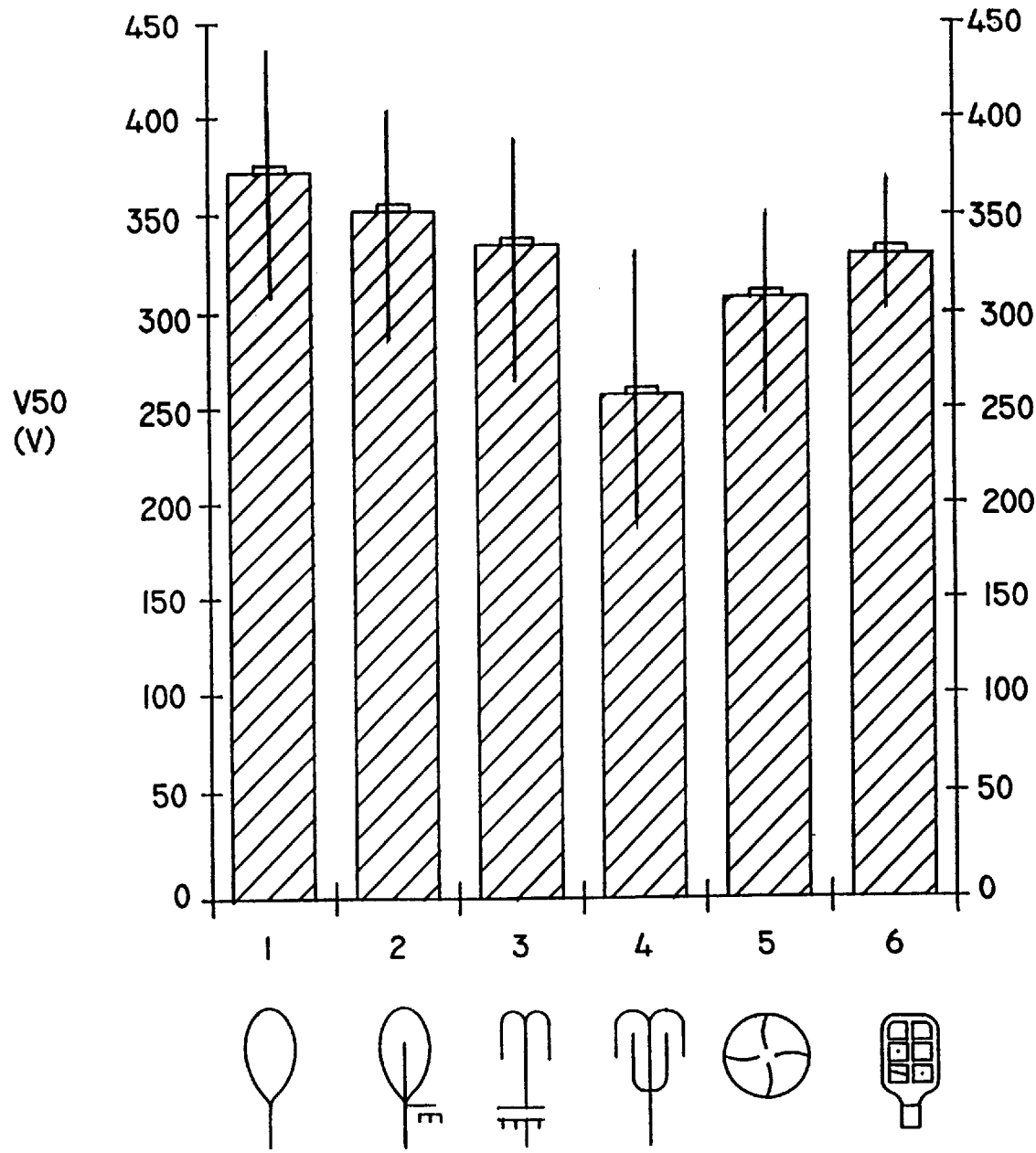
FIGS. 4 to 7 are graphs of test results for six different epicardial electrode pair configurations which were tested in five pigs.
Figure 5:
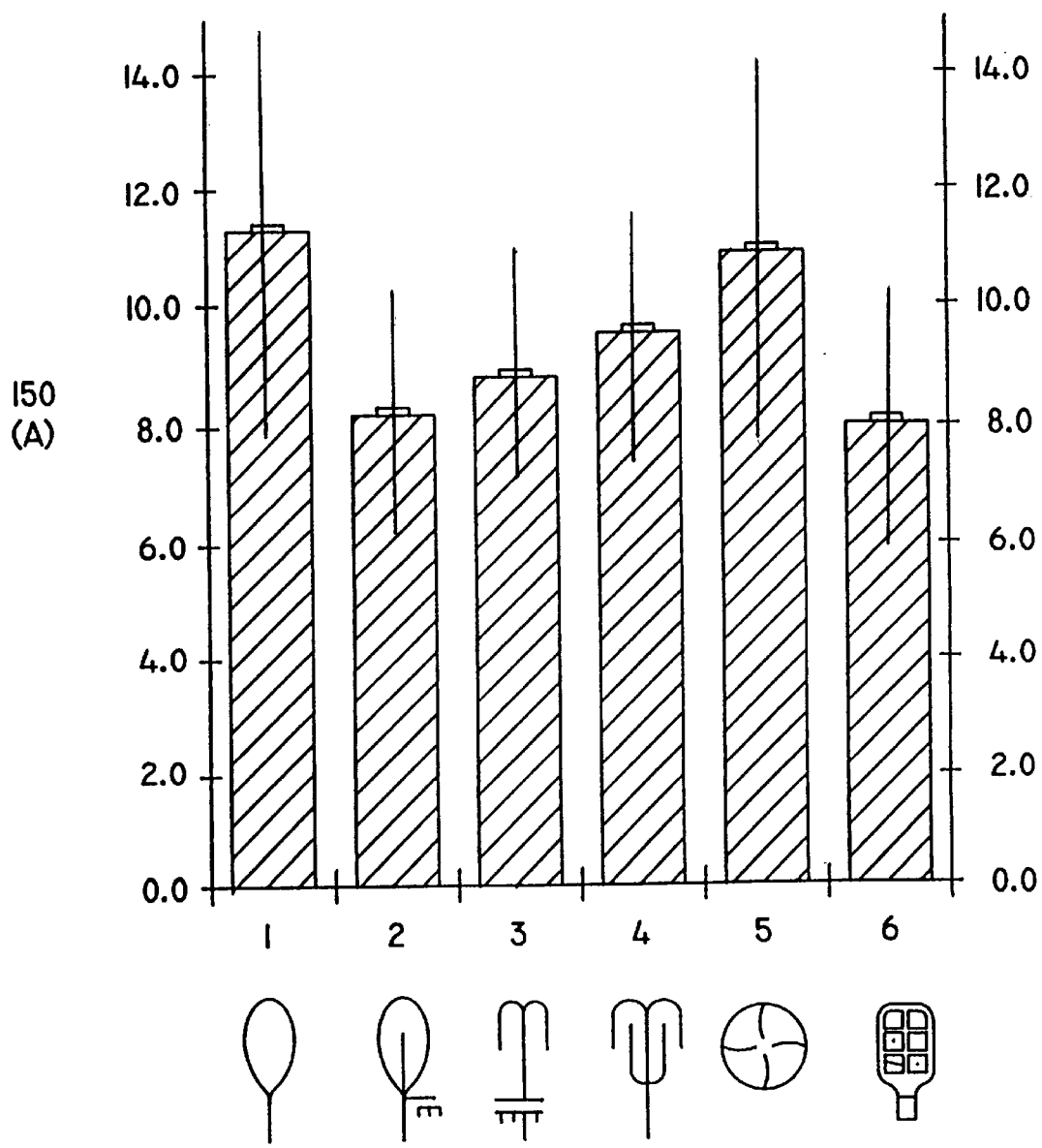
Figure 6:
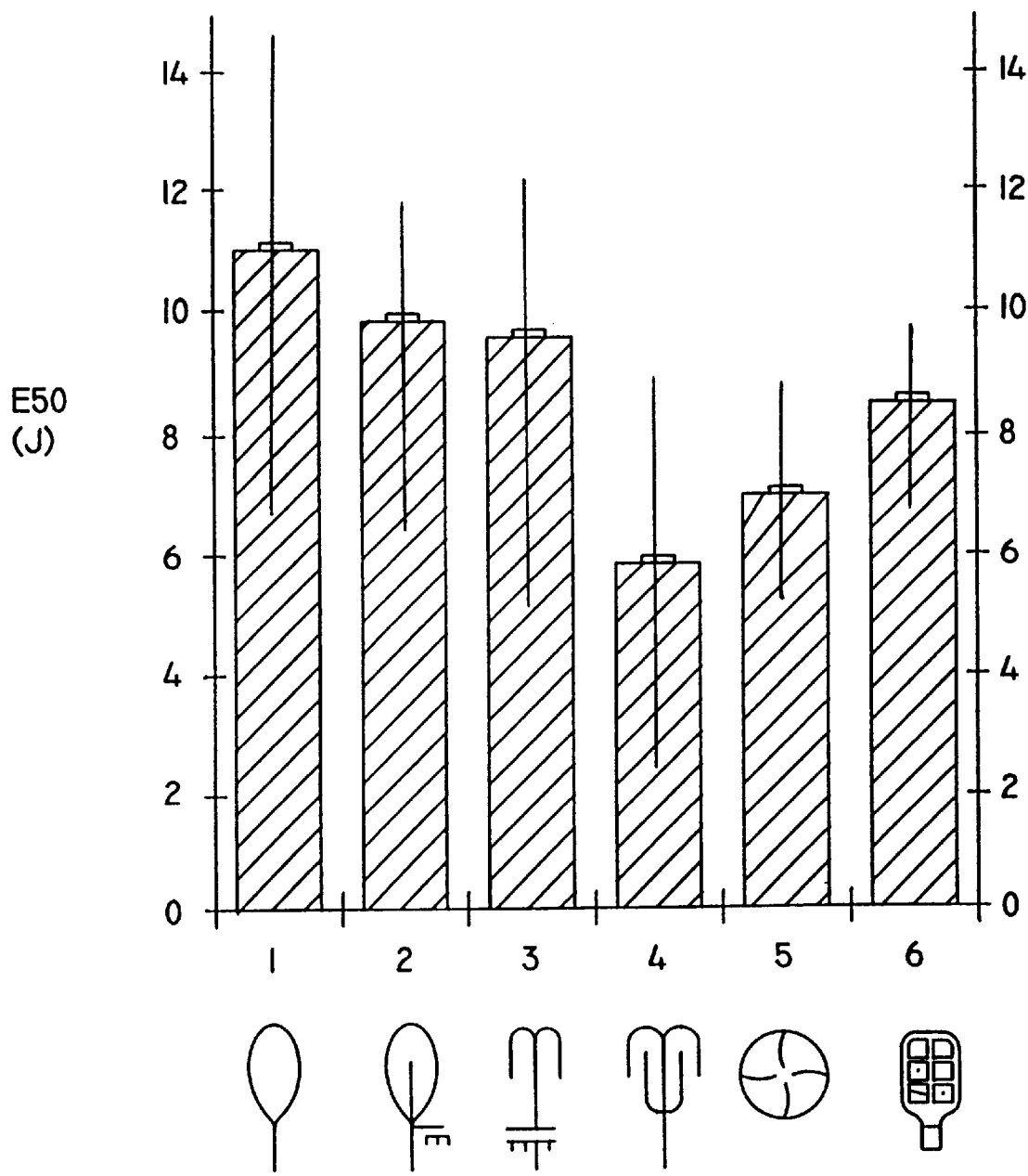
Figure 7:
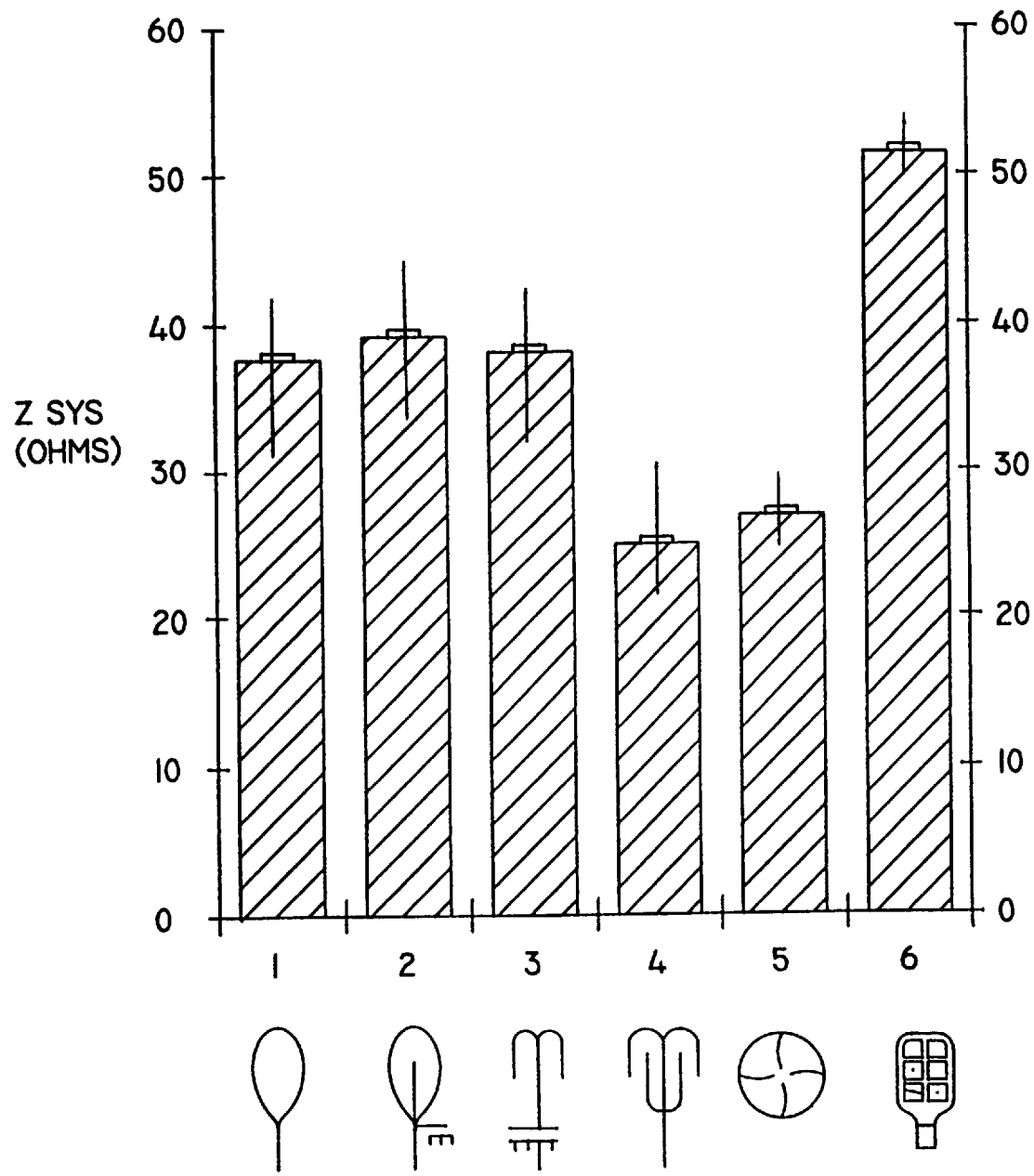

An in vivo study was performed to determine the influence of coil patch trace geometry on defibrillation strength requirements in pigs. FIGS. 4 to 6 show histograms of mean shock strength requirements described in terms of peak voltage, peak current and total energy delivered at points predicting 50% defibrillation probability in five pigs. FIG. 7 shows mean system impedance. Error bars denote one standard deviation. The term "trace geometry" is a descriptor used to define the shape and orientation of the conductive elements comprising the discharge surface of the electrode.

Significant novel features of the invention include, but need not be limited to (1) resilient elements that can be deflected during introduction to both technically simplify and decrease the invasiveness of implantation procedures, (2) resilient elements with optimum edge lengths over which shock currents are distributed, thereby reducing near-field impedance and minimizing peak voltage gradients, (3) electrode construction that does not require an insulative backing thereby producing minimal affect on transthoracic defibrillation shock strength requirements, (4) electrode structure that reduces peak voltage requirements for defibrillation by reducing near-field impedance through distribution of shock current over a large "phantom area" or "effective edge length", (5) electrode structure with interdigitating ends that space areas of high current density, (6) electrodes with spatially isolated coil elements defining open regions that conform to the dimensional excursions of the heart and thereby maintain intimate contact with subjacent heart tissue, (7) electrodes with elements that possess different resistivities to favorably alter shock-induced electric field intensities, (8) electrodes with porous backing that provide a substrate for tissue ingrowth and a plane for surgical dissection, and (9) electrode elements energized in a manner to produce different regional potentials on the electrode face.

In FIGS. 8A–8D, different sized loop style conductive electrodes are shown. By varying the length of major axis (a) and the circumference (C) of the loops, the circumscribed surface area (A) is varied.

Figure 9B:
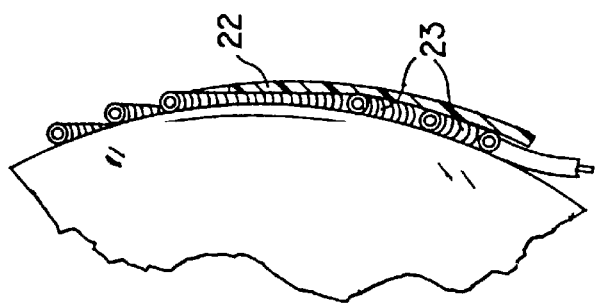
FIGS. 9A, 9A', 9A", 9B, 9B', 9C and 9C' illustrate concentric loop conductive electrodes.
FIGS. 9D and 9E illustrate a detailed view of a connection of terminal ends of coils and connection of adjacent coils to each other.
Figure 9B:
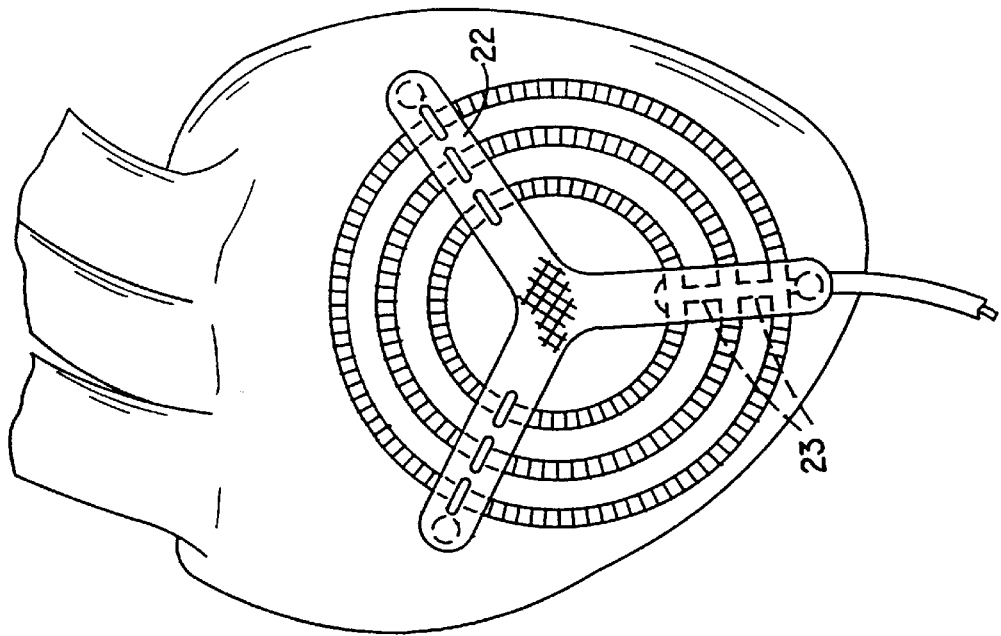
Figure 9C:
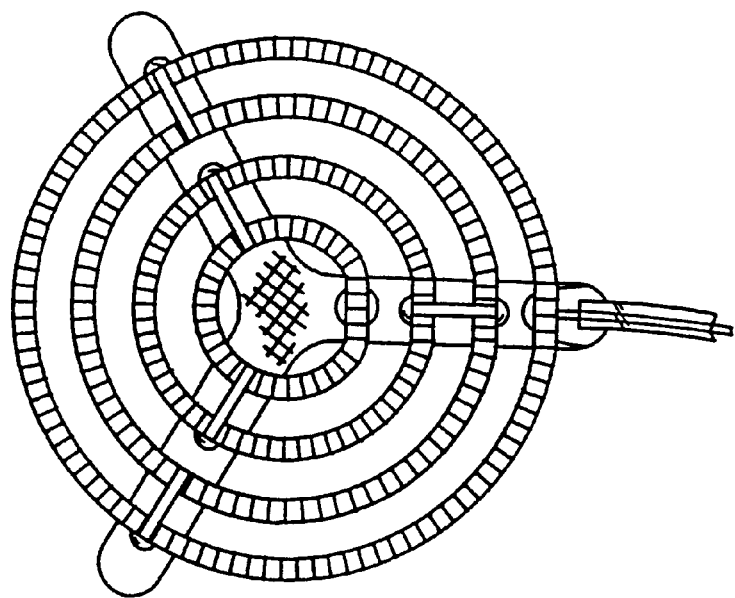
Figure 9C:
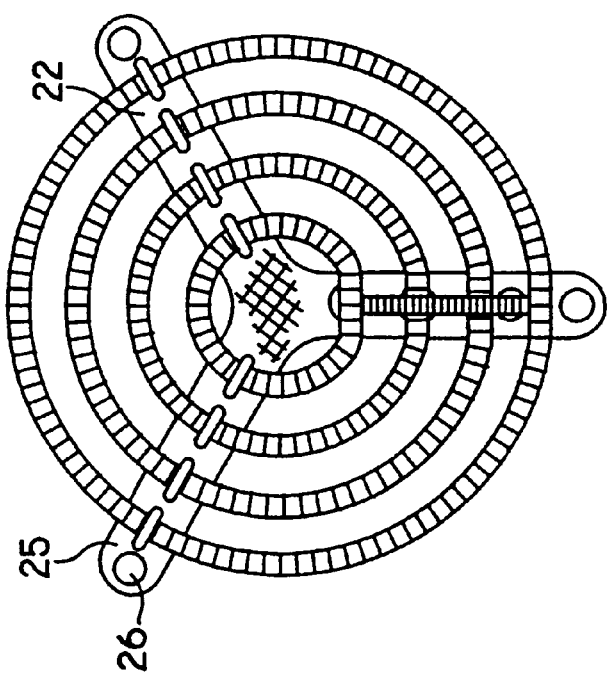

Concentric loops (normally multi-filar coils) 21 such as those shown are mounted on a three-pronged "skeletal" structure 22 (FIGS. 9A to 9C and 9C'). Typically, this structure 22 is fabricated from Dacrons® reinforced silicone rubber sheeting (0.010–0.030 inch thick, 0.1–0.5 inch wide). Electrodes fabricated in this fashion solve several problems: (1) continuous loops with smooth contours improve structural fatigue resistance, (2) defibrillation shock strength requirements are insensitive to orientation, (3) structure can be "pre-shaped" to provide radii of curvature that are coincident with typical epicardial curvatures to facilitate electrode conformation to epicardial surface as shown in FIG. 9B', (4) the high flexural compliance minimally impacts ventricular pump function, and (5) shock currents are distributed through coiled conductors that have greater surface area per unit length compared to wire mesh conductors used in conventional electrode patches.

Until now, coils have been shown attached to one side of the "skeletal" support structure 22 (FIG. 9A') to provide tangential contact of the coils 21 with the support structure 22. However, it may be advantageous to produce a structure as shown in FIG. 9A" which depicts the skeletal structure 22 between the coils 21, lying on an axis coincident with the diameter of the coils. The advantage of such a structure is that it cannot be inadvertently implanted with the conductive discharge surface side away from the heart.

Several electrode design factors are believed to influence defibrillation efficacy: (1) ratio of maximum electrode diameter to heart circumference, (2) number of elements, (3) spatial separation, and (4) means of electrical connection of elements. Two primary means of electrical connection exist: (1) connections 23 that cause the elements to be equipotential as shown in FIGS. 9A, 9B, 9C, and (2) those connections 24 that allow the current to be distributed from the innermost element to the outermost element as shown in FIG. 9C'.

The reinforced silicone rubber sheet structure 22 that serves as a "skeleton" for the electrode coil elements in many of the designs shown in the figures may be comprised of single or a plurality of arms. The ends of each arm extend beyond the major dimension of the electrode portion and form a tab 25 (FIG. 9C) thereby providing fixation means to secure the electrode portion to the underlying tissues with sutures or staples. Chronic fixation to tissues at these peripheral points may be further enhanced by incorporation of a suitable porous material 26 bonded to the tab 25 or to other areas along the "skeletal" arm. The porous material may be Dacron or other porous material that promotes stable tissue ingrowth.

With reference to FIGS. 9D and 9E, ends 25, 25' of the coil 21 are deflected, closely opposed and slid over the ends 26 of a pin 26'. Crimp sleeves 27, 27' are abutted with flanged section 28 of pin 26. The coils 21 are thereby mechanically immobilized by means of a crimp joint onto pin 26'.

Electrical connection to the other electrode elements is accomplished by means of an interconnection coil 29, which is crimped to centrally extending pin 30. This connection is illustrative of the many possible methods of connecting terminal ends of coils and connection of adjacent coils to each other.

Figure 10C:
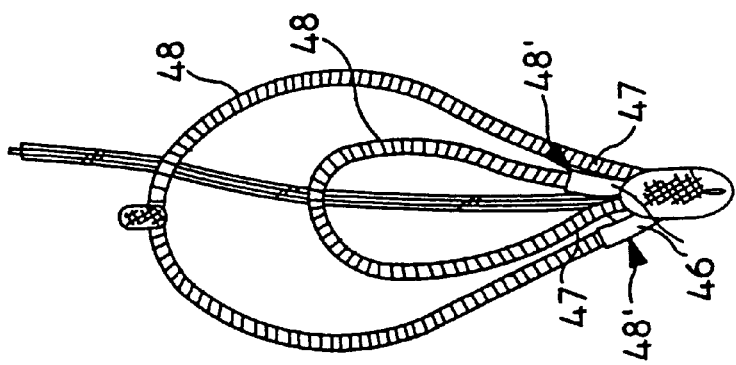
FIGS. 10A, 10A', 10B and 10C illustrate eccentric loop conductive electrodes.
FIG. 10B' is a side view of FIG. 10B.
FIGS. 10D, 10E, 10F and 10G illustrate the method of introducing a conductive electrode to the heart through a tubular applicator located in the chest wall.
Figure 10B:
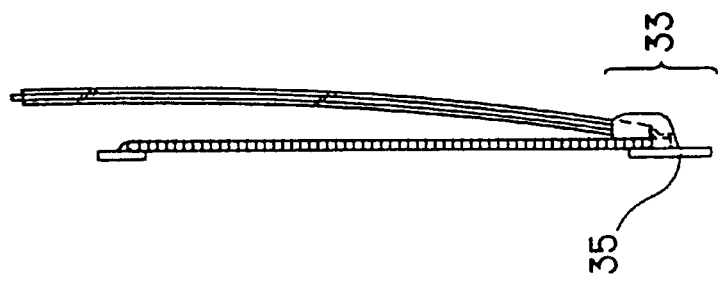
Figure 10B:
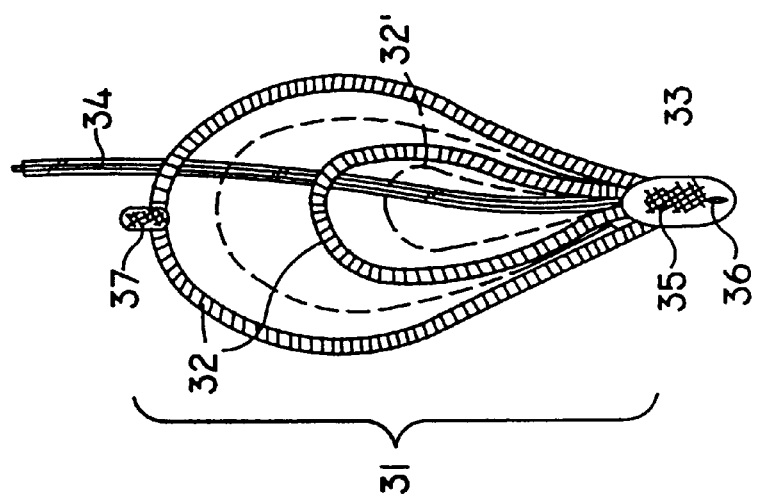
Figure 10D:
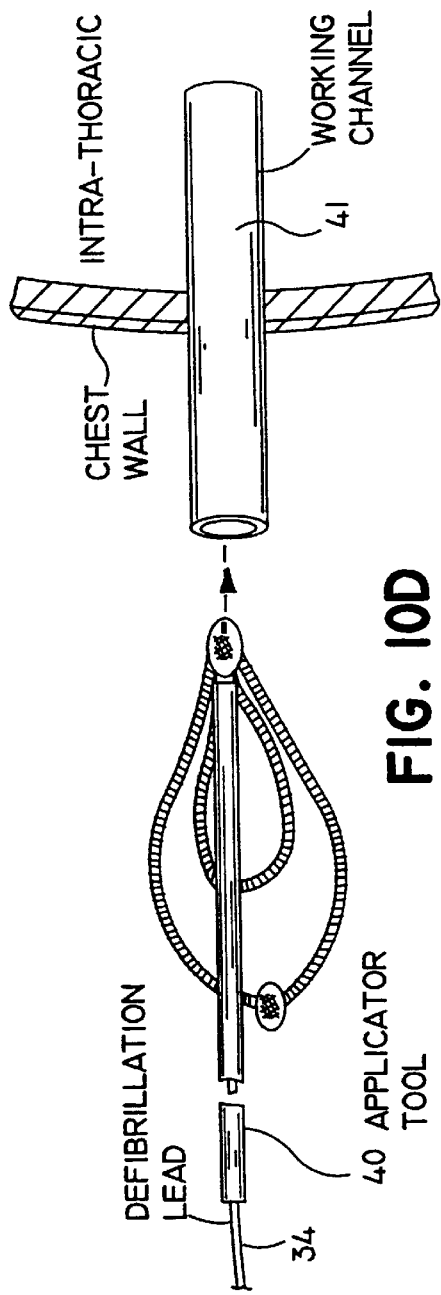
Figure 10E:
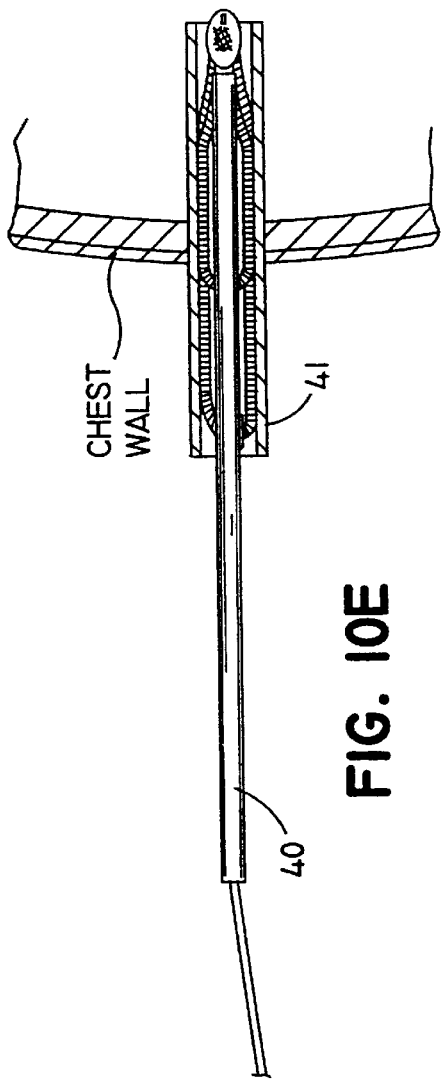

Eccentric loop structures are depicted in FIGS. 10A, 10B and 10C. This electrode structure is of particular interest because its size, shape and flexibility make it uniquely suited for implantation through the small (1 cm) tubular working channel 41 of a thoracoscopic port inserted between the ribs (normally the 4th to 6th intercostal spaces). For this specialized application, the electrode structure does not incorporate a reinforcing skeleton. In fact, the flexibility of the coils allow them to be deformed during deployment.

In one embodiment (FIG. 10A) the electrode portion 31 is formed by coils 32 that are electrically connected at a common terminal point 33. This connection area is molded over with silicone rubber and accepts the lead body 34. The distal end of the terminal portion is formed by reinforced silicone rubber sheet 35 with slit or hole 36 that provides means for fixation on or near the heart by means of conventional sutures or specialized surgical staples. Additional fixation may be provided on one or more of the coils near their proximal ends by molding a silicone boot 37 onto the electrode coil. Both fixation procedures can be performed through the working channel of the thoracoscopic port. Additional loops 32' may be beneficial as shown in FIG. 10B as phantom lines.

The novel structural orientation of the terminal end allows the electrode 31 to be introduced through the tubular working channel 41 by means of a tubular applicator 40 that coaxially passes over the lead body as shown in FIGS. 10D to 10G. The tubular applicator may be a simple, straight thermoplastic tube of appropriate wall thickness or may possess a deflected tip to assist the user in controlling electrode placement on or near the heart surface. The tubular applicator 40 engages terminal point 33 of the electrode portion and compresses coils 32 within working channel 41.

Figure 10F:
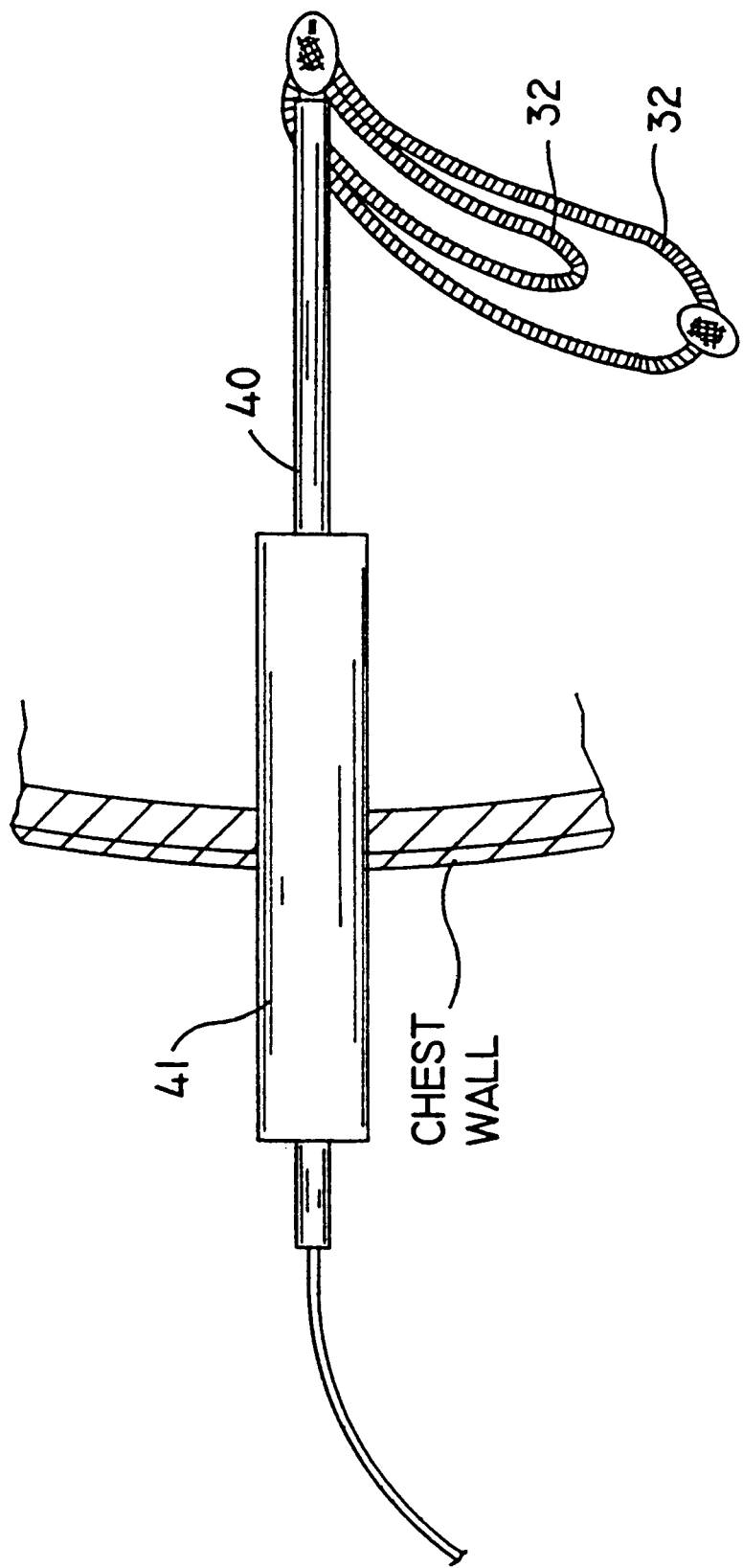
Figure 10G:
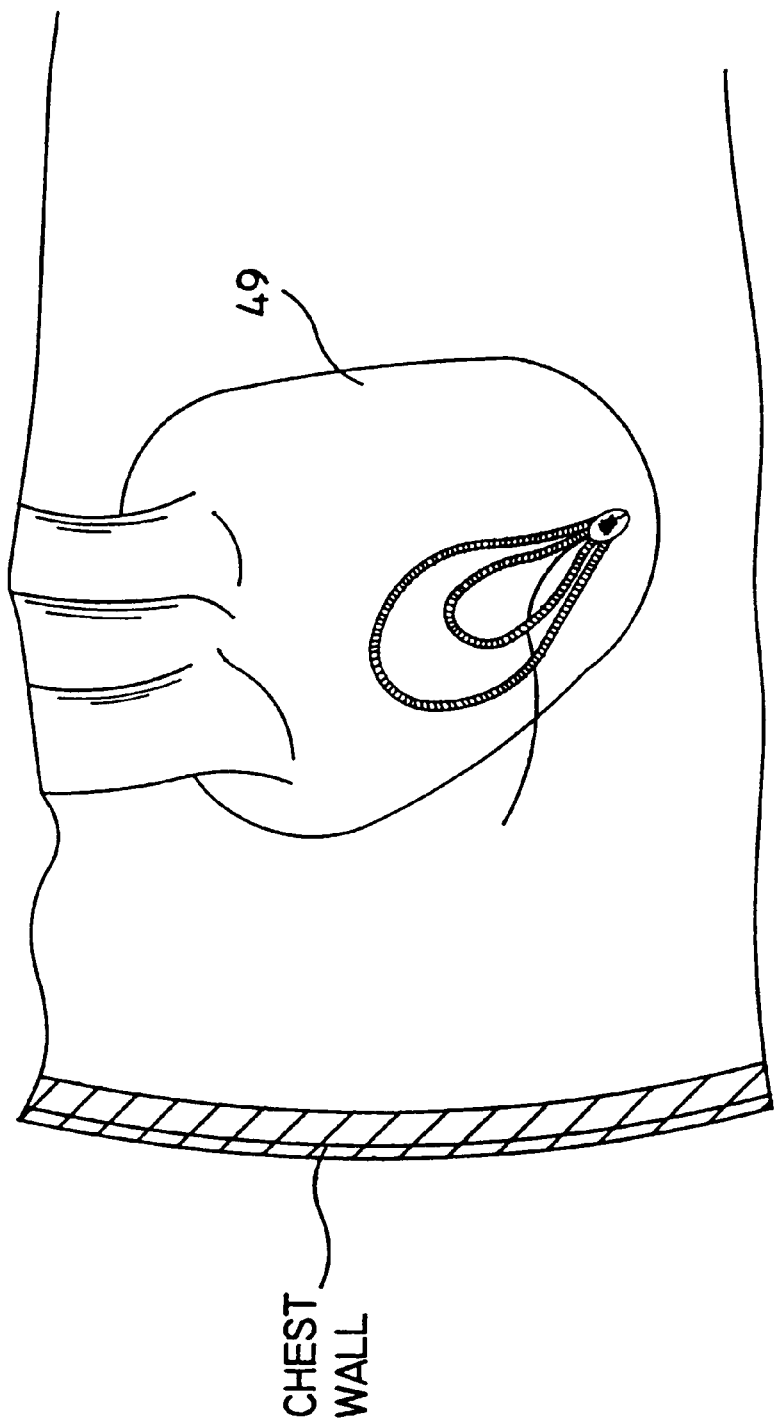

Upon passage through the working channel 41, as shown in FIG. 10F, the coils 32 resume their original form for attachment to the heart 49. Resilient biasing means within the coil elements comprising the loops may provide additional biasing force to restore the electrode portion to its unstressed shape within the body.

FIG. 10A' shows an electrode portion formed by an outer loop 38 and an inner linear coil element 39 that replaces the inner loop of FIG. 10A. This modification allows the terminal portion 33' to occupy less volume since only three coil lines are accepted instead of four. Size reduction allows the lead to be passed through small thorascopy working channels which may be important for small adult or pediatric patients. These same techniques may be applied during minimally-invasive introduction of concentric loop electrodes (9A, 9B, 9C, 9C').

In FIGS. 10A and 10B, both ends of the coils are electrically common at the terminal portion 33. An alternative embodiment (FIG. 10C) depicts an electrode portion formed by two or more eccentric coils 48 that are electrically common on their proximal ends 47, but are not electrically connected at their distal ends 46. The coils are mechanically connected, however by means of an insulting material 48' such as silicone rubber. In this way, any voltage drop is distributed along the length of the coil.

Electrode portions like those shown in FIGS. 11A, 11A', 11B and 11C are formed by spatially-isolated coil loops 50 mounted on a reinforced silicone rubber skeleton 51 similar to those previously described. Spatial isolation of the loops reduces shock impedance and improves electric field uniformity during shocks.

The structure in FIG. 11A may be deformed and inserted through the working channel of a thorascope for minimally-invasive implantation, while the three and four lobed structures shown in FIGS. 11B and 11C could be more easily implanted using an open-chest procedure. In general, it is believed that the loops should be energized from the central regions of the structure, as shown. Features described for electrodes shown in FIGS. 9A to 9C may also be implemented here.

To refine the defibrillation efficacy of the present invention, each electrode need not be symmetric. In fact, asymmetry may be advantageous for the production of favorable field intensity distributions during attempted defibrillation with electrical shocks. Since LV mass is greater than RV mass, the LV electrode should probably circumscribe a slightly larger area. Ideally, the size, shape and position of the electrodes would be optimized to minimize areas of low potential gradient within ventricular myocardium during defibrillation strength shocks.

The electrodes in a relaxed state need not be planer. Deflection of the elements in a way to form some concavity, as shown in FIG. 9B', may be beneficial in conforming to the shape of the heart.

Additionally, the electrode elements, normally electrically common, may be electrically isolated or may be constructed of materials that produce differences in the relative resistivity between the elements, thereby favorably altering the current densities along the electrode face. Segments of insulation along the electrode conductors may also enhance performance. Spacing between elements, length of elements, and position of conductor separation may all combine to influence the efficacy of electrodes disclosed by the present invention.

An alternative embodiment of the electrode configuration may include the incorporation of more than two electrodes positioned on the epicardium, or the combination of endocardial catheter electrodes with an epicardial electrode of the present invention on or near the left ventricle. Electrode polarities could be selected to produce the lowest defibrillation shock strength requirements.

Having described the invention, many modifications thereto will become apparent to those skilled in the art to which it pertains without deviation from the spirit of the invention as defined by the scope of the appended claims.

We claim:

1. A body implantable lead comprising:

an insulative lead body containing an electrically conductive element;

a first electrically conductive member formed into a loop baving a first fixation element on an apical portion of the loop and forming an electrical connection with a distal end of said electrically conductive element, said first conductive member being flexible and having an electrical discharge surface adapted to be directly contacting a heart adjacent an epicardial surface thereof but not penetrating the epicardial surface;

a second electically conductive member adapted to directly contact but not penetrate the epicardial surface of the heart, said second member being radially, mechanically connected to said first conductive member at a proximal end thereof and not mechanically connected to said first conductive member at a distal end thereof, the distal end further including a second fixation element; and an electrically insulated backing at a location where the first electrically conductive member and the second electrically conductive member are electrically connected to the electrically conductive element, the electrically insulated backing having an opening therethrough to permit the electrically insulated backing to be secured to the heart.

2. The body implantable lead according to claim 1, further comprising an insulative member having a side, and wherein said first electrically conductive member is mounted on the side of insulative member.

3. The body implantable lead according to claim 1, further comprising a plurality of electrically conductive members, radially, mechanically connected to said first conductive member at a proximal end thereof and not mechanically connected to said first conductive member at a distal end thereof.

4. The body implantable lead according to claim 1, wherein said first conductive member includes a, linear array of conductive elements.

5. A body implantable lead according to claim 1, further comprising an additional electrically conductive element extending radially inwardly from said conductive member.

* * * * *

UNITED STATES PATENT AND TRADEMARK OFFICE
CERTIFICATE OF CORRECTION

PATENT NO.: 5,916,243
DATED: June 29, 1999
INVENTOR(S): KenKnight et al.

It is certified that errors appear in the above-identified patent and that said patent is hereby corrected as shown below:

In column 9, line 12, delete "baving" and insert -- having --, therefor.

In column 10, line 12, before "insulative" insert -- the -- .

In column 10, line 21, after "a" delete -- , -- .

Signed and Sealed this

Twenty-second Day of May, 2001

Attest:

NICHOLAS P. GODICI

Attesting Officer        Acting Director of the United States Patent and Trademark Office